United States Patent [19]
Bronstein et al.

[11] Patent Number: 5,639,907
[45] Date of Patent: Jun. 17, 1997

[54] SYNTHESIS OF 1,2-DIOXETANES AND INTERMEDIATES THEREFOR

[75] Inventors: Irena Y. Bronstein, Newton; Brooks Edwards, Cambridge, both of Mass.

[73] Assignee: Tropix, Inc., Bedford, Mass.

[21] Appl. No.: 959,531

[22] Filed: Oct. 13, 1992

Related U.S. Application Data

[60] Continuation of Ser. No. 559,152, Jul. 25, 1990, abandoned, which is a division of Ser. No. 367,772, filed as PCT/US89/00016, Jan. 3, 1989, abandoned, which is a continuation-in-part of Ser. No. 140,197, Dec. 31, 1987, abandoned, which is a continuation of Ser. No. 889,823, Jul. 24, 1986.

[51] Int. Cl.$^6$ ................................................ C07C 69/00
[52] U.S. Cl. ................................................ 560/130; 560/129
[58] Field of Search ................................ 536/18.1, 4.1; 556/446; 558/195; 560/108, 141, 129, 130; 568/660

[56] References Cited

U.S. PATENT DOCUMENTS 4,962,192  10/1990  Schaap ............................ 536/18.1

*Primary Examiner*—Amelia A. Owens
*Attorney, Agent, or Firm*—Oblon, Spivak, McClelland, Maier & Neustadt, P.C.

[57] ABSTRACT

A compound of the formula

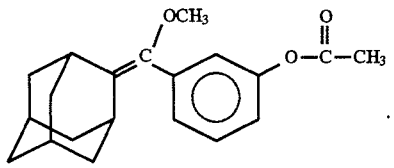

2 Claims, No Drawings

SYNTHESIS OF 1,2-DIOXETANES AND INTERMEDIATES THEREFOR

This application is a CON of Ser. No. 07/559,152 filed on Jul. 25, 1990, which is a DIV of Ser. No. 07/367,772 filed as PCT/US89/00016 on Jan. 3, 1989, which is a CIP of Ser. No. 07/140,197 filed on Dec. 31, 1987, all now abandoned, which is a CON of U.S. Ser. No. 06/889,823 filed on Jul. 24, 1986, which is pending.

BACKGROUND OF THE INVENTION

1. Field of the Invention

This invention relates generally to assay methods in which a member of a specific binding pair can be detected and quantified by means of an optically detectable reaction brought about by the enzymolysis of an enzyme-clearable group in a 1,2-dioxetane molecule. The invention relates specifically to the production of 1,2-dioxetanes and their intermediates useable in such assay methods.

2. Description of Related Art 1,2-Dioxetanes, cyclic organic peroxides whose central structure is a four-membered ring containing a pair of contiguous carbon atoms and a pair of contiguous oxygen atoms (a peroxide linkage), are a known, but heretofore seldom utilized, class of compounds. Because of their inherent chemical instability, some 1,2-dioxetanes exhibit chemiluminescent decomposition under certain conditions, e.g., by the action of enzymes, as described in copending, commonly-assigned Bronstein, U.S. patent application Ser. No. 889,823 entitled "Method of Detecting a Substance Using Enzymatically-Induced Decomposition of Dioxetanes", and in copending, commonly assigned Bronstein, et al., U.S. patent application Ser. No. 110,035 entitled "Dioxetanes for Use in Assays", the disclosures of which are incorporated herein by reference. The amount of light emitted during such chemiluminescence is a measure of the concentration of a luminescent substance which, in turn, is a measure of the concentration of its precursor 1,2-dioxetane. Thus, by measuring the intensity and duration of luminescence, the concentration of the 1,2-dioxetane (and hence the concentration of the substance being assayed, i.e., the species bound to the 1,2-dioxetane member of the specific binding pair) can be determined. The appropriate choice of substituents on the 1,2-dioxetane ring allows for the adjustment of the chemical stability off the molecule which, in turn, affords a means of controlling the onset of chemiluminescence, thereby enhancing the usefulness of the chemiluminescent behavior of such compounds for practical purposes, e.g., in chemiluminescence immunoassays and DNA probe assays.

The preparation of 1,2-dioxetanes by photooxidation of olefinic double bonds is known. However, a need exists for a convenient, general synthesis of substituted 1,2-dioxetane from olefinically unsaturated precursors derived from readily available or obtainable starting materials through tractable intermediates. In this connection, a particular need exists for a commercially useful method for producing substituted 1,2-dioxetane-B of the formula:

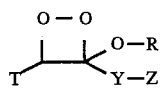

wherein T, R, Y, and Z are defined herein below, from enol ether-type precursors:

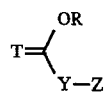

Enol ethers can be prepared by several classical methods, for example, by acid-catalyzed elimination of alcohol from acetals [R. A. Whol, "Synthesis", p. 38 (1974)], By Peterson or Wittig reactions of alkoxymethylene silanes or phosphoranes with aldehydes or ketones in basic media [Magnus, P. et al., Organometallics, 1, 553 (1982)], and by reactions of alkoxyacetic acid dianions with ketones followed by propiolactone formation and elimination of $CO_2$ [Caron, G., et al., Can. J. Chem., 51, 981 (1973)]. The O-alkylation of ketone enolate anions is less often used as a general preparative method due to the variable amounts of concomitantly formed alpha-alkylated ketones, the extent of which depends on the solvent, base, alkylating agent and ketone structure (see, M.O. Mouse, "Modern Synthetic Reactions" pp. 163–215 (Benjamin, 1965); and J. D. Roberts and M. C. Caserio, "Basic Principles of Organic Chemistry" (Benjamin, 1964)). With the use of hexamethyl phosphoramide (HMPA), a known carcinogenic solvent, it is, at best, possible to obtain yields of the O-alkylation product which are no higher than 70%. Moreover, the separation of enol ether from the C-alkylated ketones quite tedious.

SUMMARY OF THE INVENTION

Adamant-2-yl aryl ketones have been known since the late 1960's (Chem. Abst. 71:P80812V). No attempts to O-alkylate them, however, have been found in the literature. It has now been discovered that reaction of these ketones, as enolates, with reactive alkylating agents containing "hard" leaving groups [see, Fleming, I., "Frontier Orbitals and Organic Chemical Reactions", p. 40 (Wiley, 1976)], if carried out in a polar aprotic solvent such as dimethyl sulfoxide, dimethylformamide, 1,3-dimethyl-2-imidazolidinone, N-methyl-2-pyrrolidinone, and the like, or a mixture of such solvents, results exclusively in O-alkylation. The enol ethers thus obtained can be used as convenient intermediates in the synthesis of water-soluble or water compatible 1,2-dioxetanes. Such intermediates can be used to prepare substrates which react with singlet oxygen (generated chemically or photochemically) to yield 1,2-dioxetanes of sufficient stability to be useful in subsequent assay techniques based on chemiluminescent dioxetane decomposition. This O-alkylation process is general and therefore extendable to other cycloalkyl dryl ketone substrates, which can be synthesized by the reaction of the appropriate secondary cycloalkyl aldehyde with an aryl Grignard reagent, followed by oxidation of the resulting secondary alcohol with Jones reagent. Preferably, the Grignard reagent is reacted with a secondary cycloalkyl nitrile, followed by acid hydrolysis to form a ketone via an Amine salt. In all cases, starting materials and products contain a functional group attached to a secondary carbon atom of the cycloalkyl system, which in the case of fused polycycloalkyl (e.g., adamantyl) systems is flanked on either side by a bridgehead carbon atom.

It is, thus, an object of this invention to provide novel synthetic routes to enzyme-clearable 1,2-dioxetane derivatives.

It is a further object of this invention to provide processes for the preparation of novel chemical intermediates in the synthesis of 1,2-dioxetanes.

Yet another object of this invention is to provide novel compositions of matter, such as trisubstituted enolether phosphates useful as synthetic precursors of 1,2-dioxetanes which dioxetanes decompose enzymatically in an optically-detectable reaction.

These and other objects of the invention, as well as a fuller understanding of the advantages thereof, can be had by reference to the following description and claims.

DETAILED DESCRIPTION OF THE PREFERRED EMBODIMENTS

Among the 1,2-dioxetanes that can be prepared in accordance with the present invention are those having the formula:

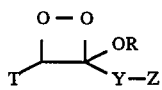

In this formula T represents a stabilizing group that prevents the dioxetane compound from decomposing before the bond in the labile ring substituent attached to Y is intentionally cleaved, such as an arl group, a heteroatom group, or a substituted cycloalkyl group having from 6 to 12 carbon atoms, inclusive, and having one or more alkoxy or alkyl substituents containing from 1 to 7 carbon atoms, inclusive, e.g., 4-tertbutyl-1-methyl-cyclohex-1-yl. The above groups can be used in any combination to satisfy the valence of the dioxetane ring carbon atom to which they are attached. Alternatively, T may be a cycloalkylidene group bonded to the 3-carbon atom of the dioxetane ring through a spiro linkage and having from 5 to 12 carbon atoms, inclusive, which may be further derivatized with one or more substituents which can be alkyl or aralkyl groups having from 1 to 7 carbon atoms, inclusive, or a heteroatom group which can be an alkoxy group having from 1 to 12 carbon atoms, inclusive, such as methoxy or ethoxy, e.g., 4-tertbutyl-2,2,6,6-tetramethyl-cyclohexyliden-1-y. The most preferred stabilizing group is a fused polycycloalkylidene group bonded to the 3-carbon atom of the dioxetane ring through a carbon—carbon or a spiro linkage and having two or more fused rings, each having from 3 to 12 carbon atoms, inclusive, e.g., an adamant-2-ylidene or an adamant-2-yl group, which may additionally contain unsaturated bonds or 1,2 fused aromatic rings, or a substituted or unsubstituted alkyl group having from 1 to 12 carbon atoms, inclusive, such as tertiary butyl or 2-cyanoethyl, or an aryl or substituted aryl group such as carboxyphenyl, or a halogen group such as chloro, or a heteroatom group which can be a hydroxyl group or a substituted or unsubstituted alkoxy or aryloxy group having from 1 to 12 carbon atoms, inclusive, such as an ethoxy, hydroxyethoxy, methoxyethoxy, carboxymethoxy, or polyethyleneoxy group.

The symbol Y represents a light-emitting fluorophore-forming fluorescent chromophore group capable of absorbing energy to form an excited energy state from which it emits optically detectable energy to return to its original energy state. Any carbon position in Y can be attached to the dioxetane ring.

Examples of suitable Y chromophores include:
1) phenylene and phenylene derivatives,.e.g., hydroxyphenyl, hydroxybiphenyl, hydroxy-9,10-5 dihydrophenanthrene;
2) naphthalene and naphthalene derivatives, e.g., 5-dimethylamino naphthalene-1-sulfonic acid, hydroxy naphthalene, naphthalimides or hydroxy naphthalimides;
3) anthracene and anthracene derivatives, e.g., 9,10-diphenylanthracene, 9-methylanthracene, 9-anthracene carboxaldehyde, hydroxyanthracenes and 9-phenylanthracene;
4) rhodamine and rhodamine derivatives, e.g., rhodols, tetraethyl rhodamine, tetraethyl rhodamine, diphenyldimethyl rhodamine, diphenyldiethyl rhodamine, and dinaphthyl rhodamine;
5) fluorescein and fluorescein derivatives, e.g., 4-or 7-hydroxyfluorescein, 6-iodoacetamido fluorescein, and fluorescein-5-maleimide;
6) eosin and eosin derivatives, e.g., hydroxy eosins, eosin-5-iodoacetamide, and eosin-5-maleimide;
7) coumarin and coumarin derivatives, e.g., 7-dialkylamino-4-methylcoumarin, 4-cyano-7-hydroxy coumarin, and 4-bromomethyl-7-hydroxycoumarin;
8) erythrosin and erythrosin derivatives, e.g., hydroxy erythrosins, erythrosin-5-iodoacetamide and erythrosin-5-maleimide;
9) benzheteroazoles and derivatives, e.g., 2-phenylbenzoxazole, hydroxy-2-phenylbenzoxazoles, hydroxy-2-phenylbenzthiazole and hydroxybenzotriazoles;
10) pyrene and pyrene derivatives, e.g., N-(1-pyrene) iodoacetamide, hydroxypyrenes, and 1-pyrenemethyl iodoacetate:
11) stilbene and stilbene derivatives, e.g., 6,6'-dibromostilbene and hydroxy stilbenes, hydroxydibenzosuberene;
12) nitrobenzoxadiazoles and nitrobenzoxadiazole derivatives, e.g., hydroxy nitrobenzoxadiazoles, 4-chloro-7-nitrobenz-2-oxa-1,3-diazol, 2-(7-nitrobenz-2-oxa-1,3-diazol-4-yl) methylaminoacetaldehyde, and 6-(7-nitrobenz-2-oxa-1,3-diazol-4-yl)aminohexanoic acid;
13) quinoline and quinoline derivatives, e.g., 6-hydroxyquinoline and 6-aminoquinoline;
14) acridine and acridine derivatives, e.g., N-methylacridine, N-phenylacridine, hyydroxyacridines, and N-methylhydroxyacridine;
15) acidoacridine and acidoacridine derivatives, e.g., 9-methylacidoacridine and hydroxy-9-methylacidoacridine;
16) carbazole and carbazole derivatives, e.g., N-methylcarbazole and hydroxy-N-methylcarbazole;
17) fluorescent cyanines, e.g., DCM (a laser dye), hydroxy cyanines, 1,6-diphenyl-,1,3,5-hexatriene, 1-(4-dimethyl aminophenyl)-6-phenylhexatriene, the corresponding 1,3-butadienes, or any hydroxy derivative of the dienes or trienes;
18) carbocyanine and carbocyanine derivatives, e.g., phenylcarbocyanine and hydroxy carbocyanines;
19) pyridinium salts, e.g., 4(4-dialkylamino styryl) N-methyl pyridinium salts and hydroxy-substituted pyridinium salts;
20) oxonols; and
21) resorofins and hydroxy resorofins.

The most suitable Y chromophores are derivatives of benzene or naphthalene:

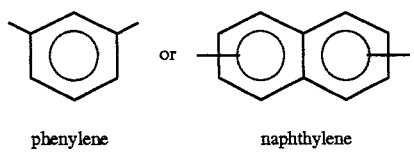

phenylene    naphthylene

The symbol Z represents hydrogen (in which case the dioxetane can be thermally cleaved via rupture of the oxygen—oxygen bond), a chemically cleavable group such as a hydroxyl group, an alkanoyl or aroyl ester group, or an alkyl or aryl silyloxy group, or an enzyme-cleavable group containing a bond cleavable by an enzyme to yield an electron-rich moiety bonded to chromophore Y, e.g., a bond which, when cleaved, yields an oxygen anion, a sulfur anion, an amine, or a nitrogen anion, and particularly an amido anion such as a sulfonamido anion.

This moiety initiates the decomposition of the dioxetane into ketone and ester fragments. Examples of electron-rich moieties include oxygen, sulfur, amine, etc. The most preferred moiety is an oxygen anion. Examples of suitable enzyme-cleavable groups include enzyme-cleavable alkanoyloxy or aroyloxy groups, e.g., an acetate ester group, or an enzyme-cleavable phosphoryloxy group, oxacarboxylate group, 1-phospho-2,3-diacylglyceride group, D-xyloside group, D-fucoside group, 1-thio-D-glucoside group, adenosine triphosphate analog group, adenosine diphosphate analog group, adenosine monophosphate analog group, adenosine analog group, α- or β-D-galactoside group, α- or β-D-glucoside group, α- or β-D-mannoside group, β-D-fructofuranoside group, β-D-glucosiduronate group, p-toluenesulfonyl-L-arginine ester group or p-toluenesulfonyl-L-arginine amide group.

The symbol R represents a $C_1$–$C_{20}$ unbranched or branched, substituted or unsubstituted, saturated or unsaturated alkyl group, e.g., methyl, allyl or isobutyl; a heteroaralkyl or aralkyl (including ethylenically unsaturated aralkyl) group, e.g., benzyl or vinylbenzyl; a polynuclear (fused ring) or heteropolynuclear aralkyl group which may be further substituted, e.g., naphthylmethyl or 2-(benzothiazol-2-yl)ethyl; a saturated or unsaturated cycloalkyl group, e.g., cyclohexyl or cyclohexenyl; a N, O, or S heteroatom containing group, e.g., 4-hydroxybutyl, methoxyethyl, or polyalkyleneoxyalkyl; an aryl group; or an enzyme labile group containing a bond cleavable by an enzyme to yield an electron rich moiety bonded to the dioxetane ring. Preferably, R is a methyl or ethyl group.

One or more of the formula components T, R, Y or Z can also include a substituent which enhances the water solubility of the 1,2-dioxetane such as a carboxylic acid, sulfonic acid or their salts, or a quaternary amino salt group.

At least one of R and Z, and preferably Z, is an enzyme clearable group, and preferably an enzyme clearable phosphate ester or glycosidic acetal group.

R may be bonded to Y to form a fused ring fluorophore-forming group which is an turn bonded to the 4-carbon atom of the dioxetane through a spiro linkage and which therefore results in an excited lactone fragment upon chemical or enzymatic dioxetane decomposition. The required enol ethers are obtained by intramolecular O-alkylation of fused polycycloalkyl aryl ketone enolates by another substituent, e.g., a toluenesulfonyloxyethyl group, in accordance with the methodology presented herein.

Y may also be further substituted with one or more electron withdrawing groups, e.g., perfluoroalkyl having from 1 to 7 carbon atoms such as trifluoromethyl; alkyl or arylsulfonyl such as methylsulfonyl; halogen such as fluoro or chloro; cyano; nitro; alkoxycarbonyl such as —COOEt; alkanoyl such as —COCH$_3$; amidosulfonyl such as —SO$_2$NHAr; or with one or more electron donating groups such as a branched or unbranched alkyl group having from 1 to 7 carbon atoms; an alkoxy or aralkoxy group having from 1 to 30 carbon atoms which may contain fused aromatic or fused heteroaromatic rings which are further substituted with heteroatom containing moieties, e.g., 2-(5-fluoresceinyl)-ethoxy; an aryloxy group having 1 or 2 rings and which may be further substituted, e.g., phenoxy; a branched or straight chain $C_1$–$C_7$ hydroxyalkyl group, e.g., hydroxymethyl or hydroxyethyl; an aryl group containing one or more hydroxy substituents or alkoxy substituents having 1 to 7 carbon atoms, e.g., 3,5-diethoxyphenyl; or a heteroaryl group having 1 or 2 rings, e.g., benzoxazole, benzthiazole, benzimidazole or benzotriazole.

Furthermore, by suitably modifying T, R, and groups of 1,2-dioxetanes, the stability of the 1,2-dioxetanes and the rate of decomposition of the 1,2-dioxetanes can be varied. For example, 1,2-dioxetanes can be attached to various molecules (e.g., proteins or haptens) or immobilizing supports (e.g., polymer membranes); they can also constitute side chain groups of homopolymers or copolymers.

More particularly, the method for producing 1,2-dioxetanes according to the present invention comprises the following reaction sequence:

I.

T—CN

↓ 1. BrMg—Y—OR$^1$
↓ 2. Acid (HW)

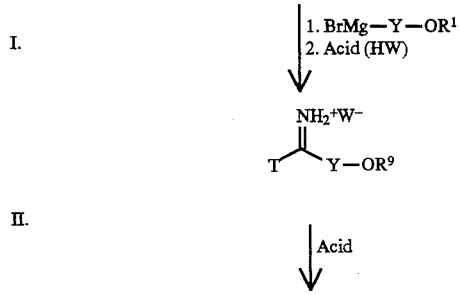

II.

↓ Acid

III.
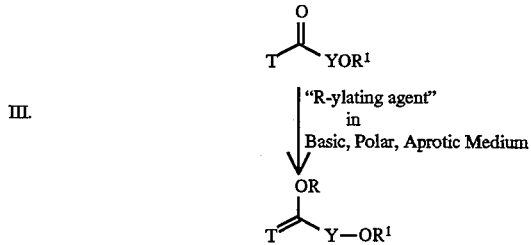
IV.
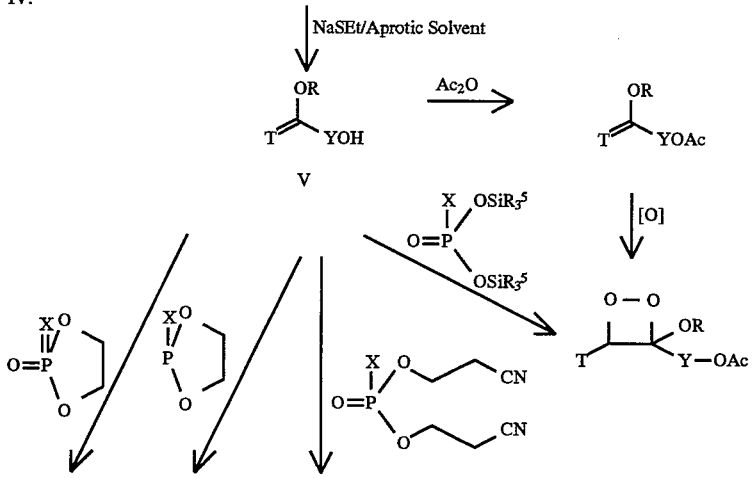
wherein $R^1$ can be independently any of the substituents as defined above for R; W is an acid anion such as halide (e.g., chloride); and X and the "R-ylating agent" are as defined below.
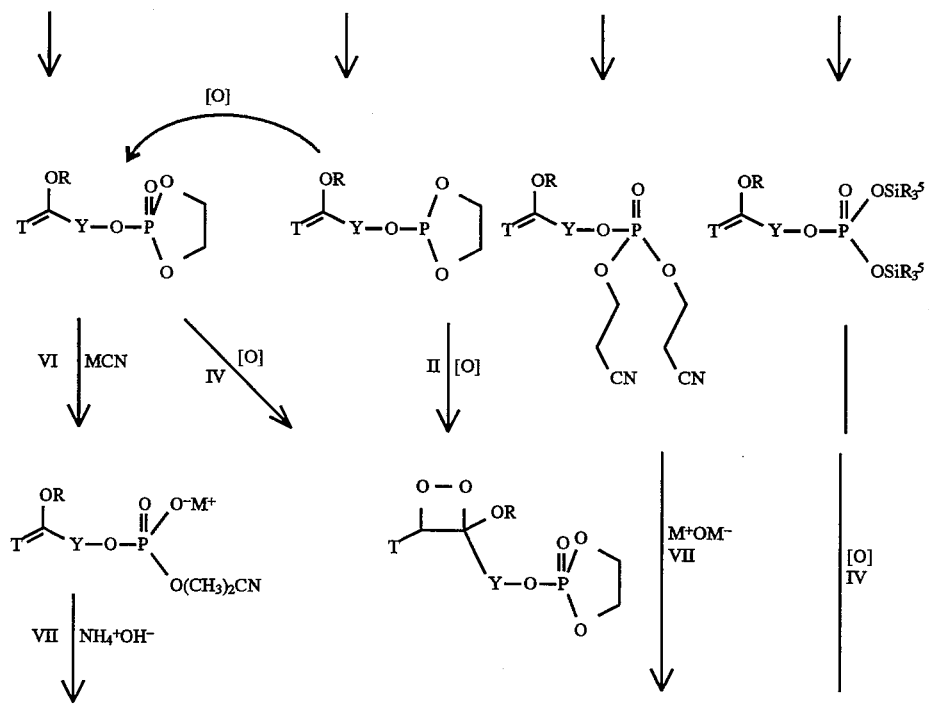

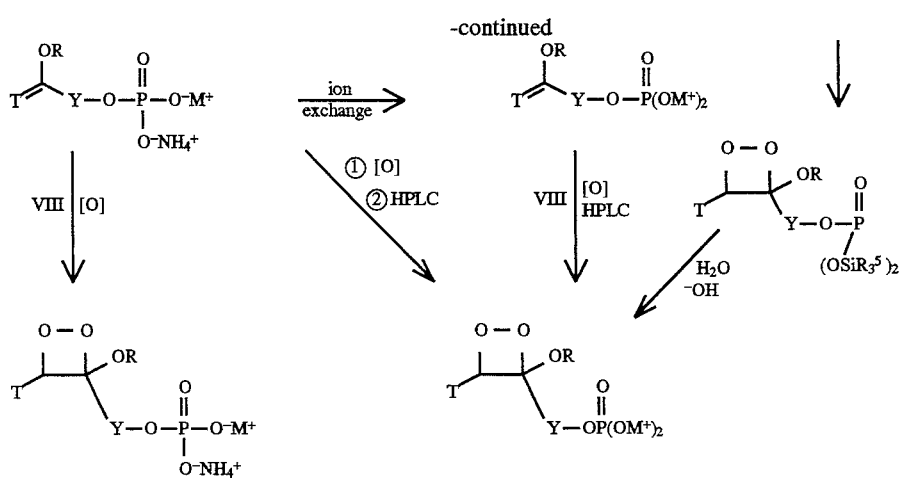

Step 1, which involves the slow attack of an aromatic Grignard reagent on a nitrile, may be run at reflux in several ethereal solvents such as diethyl ether (34°), THF (67°), or ethylene glycol dimethyl 5 ether (85°). Thus, although the reaction can be run conveniently over the temperature range of 30°–85° C., the use of THF at reflux provides optimum performance with yields above 90%. As will be understood by one skilled in the art, the use of the analogous organolithium compound to replace the Grignard reagent is possible in the above scheme, however, it is known that THF and organolithium compounds (especially n-butyllithium, the metal-halogen exchange reagent) can be incompatible at higher temperatures. Therefore, one can have recourse to the methodology described in Edwards, et al., co-pending and commonly-assigned U.S. Ser. No. 213,672, filed Jun. 30, 1988. The reaction of a fused polycycloaldehyde with an aromatic organolithium moiety allows a similar bond construction to be accomplished in diethyl ether over a temperature range of –60° to 0° C. This process then provides a convenient low temperature counterpart to the nitrile reaction, which requires only a facile, ancillary oxidation to arrive at the same ketonic product.

Step III is best accomplished in the solvents listed using sodium or potassium hydride or potassium tertbutoxide as the base. This step utilizes reactive alkylating agents to give a kinetic product and can be run conveniently over a temperature range of 0° to 60° C., depending on the "R"-ylating reagent. Dimethyl or diethyl sulfate are particularly useful and inexpensive reagents which display optimum performance between 25° and 60° C. In Step IV, the phenolic ether cleavage with sodium thioethoxide may be accomplished with soft nucleophiles such as with lithium iodide in refluxing pyridine, sodium cyanide in refluxing DMSO, or sodium sulfide in refluxing N-methyl-2-pyrrolidinone are identical in spirit while having other drawbacks from a commercial point of view.

Steps V, VI and VII, as indicated herein, may be performed separately or in one operation. The cyclic phosphorichloridate is utilized not only because of its monofunctionality, chemoselectivity, and enol ether-compatible deprotection mode, but also because, by virtue of pseudo-rotation, it is $10^6$ times more reactive than acyclic versions. Thus, in cases where an aromatic hydroxyl group is hindered (e.g., a peri position in a polycyclic, aromatic ring system), or if other substituents lower the pKb or nucleophilicity of the enol ether oxyanion, reasonable reaction rates and yields are possible. In benzene, THF, diethyl ether, or DMF, phosphate triester formation with a Lewis base, or with a preformed alkali metal salt can be effected with all of the phosphorochloridates listed over a temperature range of –30° to 50° C.

Subsequently, if a pure monosodium cyanoethyl phosphate ester is desired the ring cleavage with alkali cyanide in DMF or DMSO, should be run in a narrow temperature range between 15° and 30° C. In a one pot or in situ mode this is not important and the range widens to 60° C. on the high end.

It may be apparent that one can employ phase transfer techniques under catalysis by quaternary ammonium ions or crown ethers to generate an even more reactive "naked" cyanide and thus to utilize organic solvents of higher volatility (e.g., $CH_2Cl_2$), facilitating work-up. Alternatively, the direct use of pure, quaternary ammonium cyanides or sulfinates gives immediate access to phosphate intermediates or products which contain associated gegenions useful in modifying physical properties such as solubility. Such modifications are within the scope of the process parameters disclosed herein.

Beta-elimination processes brought to bear on the cyanoethyl substituted phosphate diester may occur under the influence of a wide range of bases. However, aqueous ammonium hydroxide can be used in vast excess due to its ease of removal at the end of the process. The cleavage can be accomplished over a temperature range of 25° to 100° C. At higher temperatures, however, provisions must be made to avoid losses of gaseous ammonia, and thus, a high-pressure vessel or bomb is required. The preferred temperature range is 35° to 55° C., where the phosphate monoester product is quite stable, and where simple glassware outfitted with wired septa can be used as a closed system. Use of alkali metal or quaternary ammonium hydroxides in this step requires close attention to stoichiometry, but as stated above, can provide a variety of mixed gegenion phosphate salts.

While chemical methods of dioxetane formation, e.g., triethylsilyl hydrotrioxide, or phosphite ozonide sources of singlet oxygen and triarylamine radical cation mediated one-electron oxidation in the presence of triplet oxygen are known, sensitized photooxygenation is a particularly convenient and forgiving process when reactive olefins are used as substrates. A variety of sensitizing dyes may be used to advantage, with chlorinated hydrocarbons comprising a preferred class of solvents. Reactions are rapid over a temperature range of –78° to 25° C. Low temperatures are not required however for these relatively stable dioxetanes, and in the case of certain phosphate salts, solubility will be reduced. The ability to manipulate gegenions directly via the synthetic methodology disclosed or in subsequent ion exchange steps permits flexibility. The preferred temperature range for all photoxygenation steps is thus 0° to 10° C.

The foregoing sequences of reactions can be carried out step-by-step with isolation of the product of each reaction. However, step VI (alkyl cleavage with a nucleophilic acidifying anion such as CN⁻ or organic sulfinate ion) and step VII (deprotection via a beta-elimination reaction) can be performed advantageously without isolation of the intermediate phosphate ester salt; such intermediate need be isolated only when it is desired to confirm its existence.

In steps VI and VII of the foregoing reaction sequence, the cation, $M^+$, in the salt used in step VI and the cation, $M^+$, in the base used in Step VII can be an alkali metal (e.g., $Na^+$), ammonium, or a $C_1$–$C_7$ alkyl, aralkyl, or aromatic quaternary ammonium cation, $(NR_4)^+$ (wherein $R_4$ can be any or all of an alkyl, e.g., ethyl, aralkyl, e.g., benzyl, or form part of a heterocyclic ring system, e.g., pyridinium), so that the products of steps VII and VIII would be as follows:

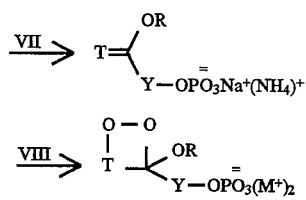

In addition, the quaternary ammonium cation can be connected through one of its quaternizing groups to a polymeric backbone, as follows:

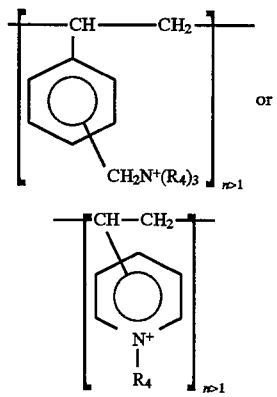

or can itself be part of a polyquaternary ammonium salt. $M^+$ can also be a fluorescent onium moiety such as a substituted benzopyrillium or 2-[4-dimethylaminostyryl]-N-methylpyridinium counterion.

Within the framework of the foregoing synthesis, the present invention comprises a process for producing a compound having the formula:

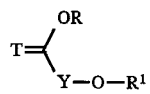

wherein T=, R, $R^1$ and Y are defined above, by reacting a compound having the formula:

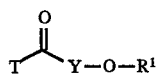

wherein T is spiro bound at a carbon atom alpha to the carbonyl group, with an alkylating agent (or in more general terms consistent with the definition of R, an "R-ylating agent") selected from the group including R-sulfate, toluenesulfonate ("Tosylate"), methanesulfonate ("mesylate"), trifluoromethanesulfonate ("triflate"), and chloromethyl ethers and trialkyloxonium salts, in a basic, polar, aprotic medium, for example, an alkali metal alkoxide in dimethyl sulfoxide.

The invention further provides a process for producing a compound having the formula:

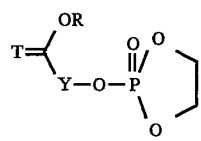

wherein T, R, and Y are as defined above, comprising reacting a compound having the formula:

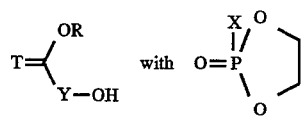

wherein X is an electronegative leaving group such as halogen (e.g., chloro), in the presence of a Lewis base such as a tertiary amine (e.g., triethylamine) dissolved in an aprotic organic solvent, such as an aromatic liquid (e.g., benzene, toluene), and ether (e.g., glyme, diglyme) or a cyclic ether (e.g., tetrahydrofuran ("THF")).

In a one-pot process, where synthesis of a phosphate triester and subsequent deprotection to a monoester are done in situ, it is advantageous to preform an alkali metal salt of the aforementioned Y—OH compound in a polar, aprotic solvent such as dimethylformamide, using NaH as the base (see Example 16 below). Addition of the phosphorochloridate affords a solution of the triester which can be directly converted (⁻CN, $NH_4OH$) to the monoester in the same reaction medium.

As an alternative to the use of halophosphate, the analogous halophosphites, i.e., $XPO_2(CH_2)_2$, can be used with subsequent oxidation and irradiation to form the dioxetane directly.

In another aspect, the invention provides a process for producing compounds having the formulas:

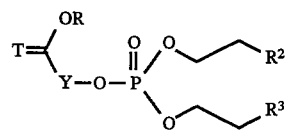

or

-continued

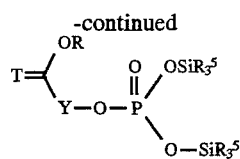

wherein T, R and Y are as defined above, $R^5$ can be independent of any of the substituents described above for R, and $R^2$ and $R^3$ are each independently cyano, ortho- or para-nitrophenyl, ortho, para- or ortho, ortho'-dinitrophenyl, comprising reacting a compound having the formula:

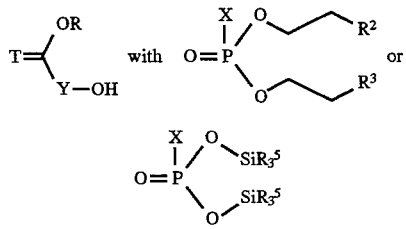

wherein X is as defined above, in the presence of a Lewis base such as a tertiary amine (e.g., a trialkylamine) in an aprotic organic solvent such as an aromatic liquid (e.g., benzene or toluene), an ether (e.g., glyme, diglyme) or a cyclic ether (e.g., THF). As an alternative to the use of halophosphates, the analogous nor-oxy compounds (i.e., halophosphites) can be used, followed by oxidation at the phosphorous, deprotection and photooxidation to the dioxetane. In the case of the cyclic phosphite, dioxetane formation and oxidation at the phosphorous can occur simultaneously in the presence of $^3O_2/^1O_2$ mixtures found in the photooxidation reaction.

Preferably, the oxidation described above is effected photochemically by treating the olefin with singlet oxygen ($^1O_2$) in the presence of light. $^1O_2$ adds across the double bond to form the dioxetane as follows:

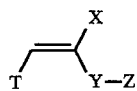

The reaction is preferably carried out at or below 0° C. in a halogenated solvent, e.g., methylene chloride. $^1O_2$ can be generated using a photosensitizer. As photosensitizers, polymer-bound Rose Bengal (commercially known as Sensitox I and available from Hydron Laboratories, New Brunswick, N.J.) and methylene blue (a well-known dye and pH indicator) or TPP (see Example 17 below) can be used.

Within the framework of the foregoing syntheses, the present invention also comprises a process for producing a compound of the general structure:

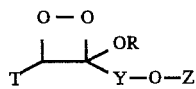

wherein R, T and Y are as defined above, and Z is a D-sugar molecule linked to Y via a glycosidic linkage, by first reacting a component of the following general structure:

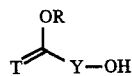

wherein Y is a phenyl or naphthyl group, with a tetra-O-acetyl-D-hexopyranosyl halide to produce an intermediate of the following general structure:

As will be appreciated by one skilled in the art, there are other methods available for the synthesis of glycosides as the α or β isomers. The use of the acetoxyhalosugars as glycosyl donors in this particular stereoselective mode is illustrative only.

In the second reaction, the acetate protective groups are removed by hydrolysis to produce the following general structure:

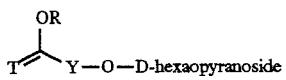

In the third reaction, the photochemical oxidation reaction described above is applied to the above intermediate to produce as a product:

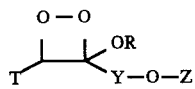

wherein T and X are described above, Y is a fluorophore such as a phenyl or naphthyl moiety, and Z is a sugar linked to Y via an α or β glycosidic bond.

The dioxetanes of the invention provide a method for generation of light in an optically detectable assay method to determine the presence or concentration of a particular substance in a sample. Examples of such assays include immunoassays to detect antibodies or antigens (e.g., hormones such as α or β-hCG, TSH, LH, etc., cancer-associated antigens such as AFP and CEA) (enzyme-immunoassay); enzyme assays (e.g., alkaline phosphatases and α- or β-D-galactosidases); chemical assays to detect cations, e.g., potassium or sodium ions; and nucleotide probe assays to detect, e.g., viruses (e.g., HSVI, HTLV III, hepatitis virus, cytomegalovirus), or bacteria (e.g., E. coli )).

When the detectable substance is an antibody, antigen, or nucleic acid, the enzyme capable of cleaving group Z of the dioxetane is preferably bonded to a substance (i.e. a substance that binds specifically to the detectable substance), e.g., an antigen, antibody, or nucleic acid probe, respectively. Conventional methods, e.g., carbodiimide coupling, are used to bond the enzyme to the specific affinity substance; bonding is preferably through an amide linkage.

In general, assays are performed as follows. A sample suspected of containing a detectable substance (e.g., antigen) is contacted with a buffered solution containing an enzyme bonded to a substance having a specific affinity for the detectable substance (e.g., antibody). The resulting solution is contacted with a solid phase, e.g., antibody-binding beads, to which another substance having the specific affinity, e.g., antibody, is bound. After incubation for a certain period, excess enzyme which is bound to be substance with specific affinity is then washed away, and a 1,2-dioxetane (substrate) having a group Z that is cleavable by the enzyme portion is added. The enzyme cleaves group Z, causing the dioxetane to decompose into ketone and ester moieties; chromophore Y bonded to the ester is thus excited and luminesces. Luminescence is detected using, e.g., a cuvette or camera luminometer, as an indication of the presence of the detectable substance in the sample. Luminescence intensity is measured to determine the concentration of the substance.

When the detectable substance is an enzyme, a specific affinity substance (e.g., antibody) is not necessary. Instead, 1,2-dioxetanes having a Z group that is clearable by the enzyme being detected is used. Therefore, an assay for the enzyme involves adding 1,2-dioxetanes to the enzyme-containing sample, and detecting the resulting luminescence as an indication of the presence and the concentration of the enzyme.

The following examples are intended to illustrate the invention in detail, but they are in no way to be taken as limiting, and the present invention is intended to encompass modifications and variations of these examples within the framework of their contents.

EXAMPLE 1

3-Methoxyphenyl adamant-2-yl-ketone

Magnesium turnings (1.64 g, 0.067 mol) were placed in a flame-dried flask under argon. A small crystal of iodine and 7 ml of dry tetrahydrofuran ("THF") (freshly distilled over lithium aluminum hydride) was added. A quantity (7 ml, 0.055 mol) of 3-bromoanisole was added by syringe to the slightly agitated suspension of the metal. An exothermic reaction began after brief heating to 50° C. The flask was placed in a water bath at room temperature while THF (33 ml) was added in a thin stream from an addition funnel. After the exothermic reaction had subsided, the mixture was refluxed for 45 minutes. A solution of 2-cyanoadamantane (8.7 g, 0.054 mol; see, "Organic Syntheses", 57, 8 (Wiley, 1977) or van Leusen, A. M. et al., J. Org. Chem., 42, 3114 (1977)) in 50 ml of dry THF was added dropwise over 1.5 hours to the refluxing Grignard reagent. After heating the reaction mixture at reflux temperature overnight, a yellow suspension was obtained. Ether (50 ml) was added, while the flask and its contents were cooled in an ice bath. Concentrated hydrochloric acid (8 ml, 0.096 mol HCl) was added dropwise with vigorous stirring over a period of 20 minutes. The precipitate was separated by filtration, washed with ether, and dried to obtain 29 g of the ketenimine salt as a light, buff-colored, non-hygroscopic powder containing some residual magnesium. The salt was suspended in a mixture of 90 ml of ethanol and 90 ml of concentrated hydrochloric acid and refluxed for 3 hours, during which time the mixture became considerably thinner. After cooling in an ice bath, the resulting solid was broken up, separated by filtration, washed to neutrality and dried to obtain 13.65 g (93% yield based on 2-cyanoadamantane) of the light gray ketone (m.p. 111°–114°C.). Thin layer chromatography ("TLC") indicated that the product was sufficiently pure for subsequent manipulation ($R_f$ 0.45; Whatman K5F $CH_2Cl_2$: hexanes, 50:50). Recrystallization from hexanes yielded the captioned compound as prismatic crystals (m.p. 113°–115° C.). I.R. ($CH_2Cl_2$): 2900 $cm^{-1}$, 1670 $cm^{-1}$ (C=O), 1590 $cm^{-1}$, 1575 $cm^{-1}$. $^1$H-NMR (400 MHz, $CDCl_3$): δ 1.55–2.05 (m, 12H); 2.30 (s, 2H); 3.41 (s, 1H); 3.84 (s, 3H); 7.03–7.40 (m, 4H). These data confirmed the following structure:

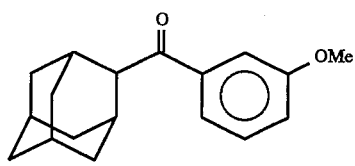

EXAMPLE 2

Methoxy(3-methoxyphenyl)methylene adamantane

A quantity (11.3 g, 0.042 mol) of 3-methoxyphenyl adamant-2-yl ketone obtained according to Example 1 was suspended in 90 ml of molecular sieve-dried (3 Å) dimethylsulfoxide (DMSO). Heat was applied to dissolve the suspended solid. Upon cooling to room temperature with stirring, a fine suspension was formed. Potassium tertbutoxide (8.5 g, 0.070 mol) was added under an argon atmosphere. After 5 minutes, a nearly homogenous orange solution resulted, which was placed in a water bath at 50° C. Dimethyl sulfate (4 ml, 0.042 mol) was added dropwise by syringe over a period of 10 minutes. After 15 minutes of further stirring, an additional 3.3 ml of dimethyl sulfate (0.034 mol) was added in the same fashion. Subsequently, the colorless solution was stirred overnight at room temperature. After cooling in an ice bath, 0.5 g of $K_2CO_3$ and 125 ml of ice water added and the mixture extracted with three 50 ml portions of ethyl acetate. The combined organic fractions were washed with three portions of water, once with 50 ml of saturated aqueous NaCl solution, and dried over $K_2CO_3$. The solvent was removed in vacuo to yield an oil. The oil was dissolved in hexane, and the resulting solution filtered through Celite and concentrated in vacuo to provide 11.5 g (96% yield) of a viscous, straw-colored oily substance. TLC indicated a clean conversion to an enol ether ($R_f$ 0.68; E. Merck $Al_2O_3$—$CH_2Cl_2$: hexanes - 50:50) with a trace of the ketone starting material. The oil was distilled from $K_2CO_3$ (b.p. 148°–150° C., 0.25 mm Hg). Under these conditions, slight yellowing occurred in the still head. I.R. analysis of this distillate revealed a small ketone absorption band at 1670 $cm^{-1}$. I.R. ($CH_2Cl_2$): 2900 $cm^{-1}$, 1670 $cm^{-1}$ (weak), 1600 $cm^{-1}$, 1590 $cm^{-1}$, 1580 $cm^{-1}$, 1570 $cm^{-1}$, 1095 $cm^{-1}$, 1080 $cm^{-1}$; $^1$H-NMR 60 MHz ($CDCl_3$): δ 1.5–2.0 (m, 12H), δ 2.55 (s,—1H) δ 3.2 (s, 1H), δ 3.25 (s, 3H), δ 6 3.75 (s, 3H), and δ 6.7–7.3 (m, 4H). These data confirmed that the structure of the product was:

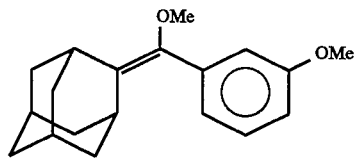

EXAMPLE 3

Methoxy(3-hydroxyphenyl)methylene adamantane

A solution of methoxy(3-methoxyphenyl)methylene adamantane (14 g, 0.049 mol), obtained according to Example 2, in 70 ml of molecular sieve-dried (3 Å) dimethylformamide (DMF) was added under an argon atmosphere to a solution of sodium thioethoxide (7.4 g, 0.88 mol) in the same solvent. The mixture was refluxed for 3 hours. After cooling in an ice bath with stirring, the reaction was quenched with 62 g of NH₄Cl in 200 ml of water. Ethyl acetate (120 ml) and a small amount of ice water were added. The aqueous layer was separated and extracted with 75 ml of ethyl acetate. The organic extract was washed with four 100 ml portions of water, then with saturated NaCl solution (100 ml), and quickly dried over Na₂SO₄. The solution was filtered and concentrated to an oily substance which was then triturated with 50 ml of hexanes. Upon removal of the solvent on a rotary evaporator, a solid separated, which was then triturated with cold hexanes, filtered and washed with hexanes. The crude, off-white phenolic product (13 g) was recrystallized from 5% MeOH in CH₃CN to yield 10 g of colorless prismatic crystals (m.p. 131°–133° C.). I.R. (CH₂Cl₂): 3580 cm⁻¹, 3320 cm⁻¹, 2910 cm⁻¹, 1590 cm⁻¹, 1580 cm⁻¹, 1440 cm⁻¹. ¹H-NMR (400 MHz, CDCl₃): δ 1.70–1.91 (m, 12H); 2.58 (s, 1H); 3.18 (s, 1H); 3.26 (s, 3H); 5.25 (s, 1H); 6.70–7.20 (m, 4H). These data confirm the following structure:

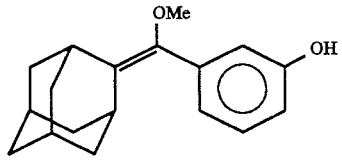

EXAMPLE 4

Ammonium sodium 3-(adamantylidenemethoxymethyl) phenyl phosphate

A quantity (1.1 g, 0.004 mole) of methoxy(3-hydroxyphenyl)methylene adamantane, obtained according to Example 3, was dissolved in 15 ml of molecular sieve-dried (3 Å) benzene under argon. Triethylamine (0.57 ml, 0.004 mole) was added via syringe. The stirred solution was cooled to 0° C. in an ice bath for dropwise addition of 2-chloro-2-oxo-1,3,2-dioxaphospholane (0.37 ml, 0.004 mole). After 10 minutes in the cold bath, the viscous mixture was slowly warmed to room temperature and stirred for 3.5 hours. The benzene was removed in vacuo, and 60 ml of ether was added under argon. The suspension was filtered under an inert atmosphere, and the resulting solid washed with three 20 ml portions of ether. The filtrate was removed in vacuo to yield 1.6 g of the phosphate triester as a colorless, viscous oily substance which was moisture sensitive. I.R. (CH₂Cl₂): 2900 cm⁻¹, 1600 cm⁻¹, 1575 cm⁻¹, 1300 cm⁻¹ (P═O). No phenolic OH stretching or C═O (1670 cm⁻¹) absorption was present in the I.R. spectrum. TLC showed the absence of the starting material. These data are consistent with the following structure of 3-(adamantylidenemethoxymethyl) phenyl ethylene phosphate:

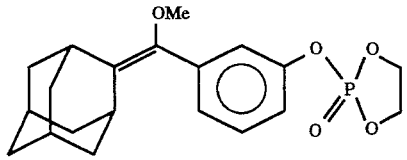

The oily substance obtained above was dissolved in 7 ml of DMF, sodium cyanide (0.21 g, 0.004 mole) was added, and the mixture stirred for 24 hours at room temperature. The solvent of the resulting yellow solution was distilled off at 50° C. in vacuo and further removed by chasing several times with 2 ml portions of xylene. The residue was triturated with ether to produce a gum, which was mixed with CH₂Cl₂, filtered and stripped in vacuo to yield 1.5 g of a light yellow, amorphous foam. I.R. (CH₂Cl₂): 2240 cm⁻¹ (weak, CN), 1595 cm⁻¹, 1570 cm⁻¹, 1475 cm⁻¹, 1275 cm⁻¹(P═O), 1235 cm⁻¹ 1100 cm⁻¹. These data are consistent with the following expected structure of sodium 3-(adamantylidenemethoxymethyl)phenyl-2'-cyanoethyl phosphate:

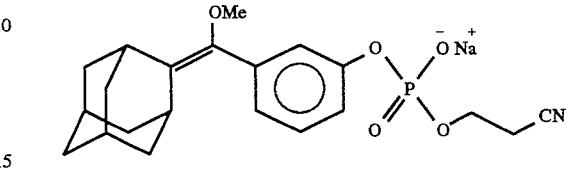

This salt (1.5 g, 0.0035 mole) was dissolved in 5 ml of water. Concentrated ammonium hydroxide (5 ml) was then added dropwise. The solution was stirred overnight at room temperature. The resulting white slurry was cooled in an ice bath and treated with 30 ml of acetonitrile. Filtration and washing with two 15 ml portions of cold acetonitrile afforded 0.95 g of a hygroscopic, white solid (sintered at 115° C., melted at 130°–133° C.) after brief drying under vacuum. HPLC (reverse phase C18—0.1% ammonium acetate/CH₃CN) gradient) showed one major peak. I.R. (Nujol): 1595 cm⁻¹, 1575 cm⁻¹, 1245 cm⁻¹, 1200 cm⁻¹, 1095 cm⁻¹, 1080 cm⁻¹, 890 cm⁻¹, U.V. (20% MeOH-dioxane) max 260/nm.; ∈=10,000. ¹H-NMR (400 MHz, D2O): δ 1.60–1.80 (m, 12H); 2.44 (s, 1H); 2.97 (s, 1H); 3.22 (s, 1H); 4.65 (s, HOD); 6.88–7.20 (m, 4H). These data confirmed that the structure of the product was:

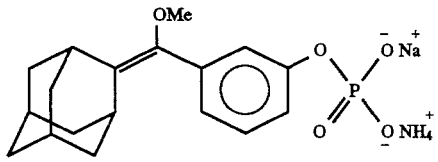

EXAMPLE 5

3-(2'-spiroadamantane)-4-methoxy-4-(3"-phosphoryloxy)phenyl-1,2 dioxetane, sodium ammonium salt In a large culture tube, 0.065 g (0.00017 mole) of the enolether phosphate salt, obtained according to Example 4, was dissolved in 25 ml of CHCl₃. A quantity (0.210 g) of methylene blue on silica gel (0.0026 g dye/g SiO₂) was added as a sensitizer. The tube was placed in a silvered Dewar flask containing a 250 watt, high-pressure sodium lamp inside a water-cooled immersion well. A piece of 5 mil Kapton® (Dupont) was placed inside the well as a U.V. filter. Ice water was pumped through the apparatus to maintain the sample temperature below 10° C. A continuous stream of dry oxygen was passed into the reaction vessel through a capillary tube. The gas flow was adjusted so as to just maintain a uniform suspension of the solid-phase sensitizer. After 25 minutes of irradiation time, the U.V. (260 nm) absorption of the starting material disappeared. The light yellow solution was filtered, evaporated, and reconstituted with 10 ml water. The aqueous sample was filtered through a 0.45 micron nylon filter and chromatographed on a reverse phase, C18 preparative HPLC column using a water/acetonitrile gradient. The fractions showing weak U.V. absorption at 277 nm were combined and lyophilized to provide the dioxetane as a white, cotton-like, hygroscopic solid.

AMPPD Na$^+$NH$_4^+$ salt did not exhibit a melting point. Instead, subliming vaporization occurred between 145°–150° C. A solid residue remained which partially decomposes but did not melt below 270° C.

$^1$H N.M.R. (D$_2$O, ppm): 0.89–1.85 (m, 12H); 2.10 (s, 1H); 2.75 (s, 1H); 3.15 (s, 3H); 4.65 (s, HOD-NH$_4^+$); 7.10–7.36 (m, 4H).

I.R. (Nujol mull, cm$^{-1}$): 3120, 1970–1790 (weak, broad-NH$_4^+$), 1640 (broad), 1600 (weak), 1580, 1284, 1273, 1122, 980, 895.

The structure of the product was thus confirmed as being:

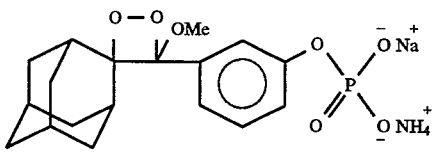

EXAMPLE 6

3-(2'-spiroadamantane)-4-methoxy-4-(3"-phosphoryloxy)phenyl-1,2-dioxetane, disodium salt Methoxy (3-phosphoryloxyphenyl)methylene adamantane sodium ammonium salt (3.3 g) was dissolved in 15 ml of water containing a drop of pyridine. The solution was slowly run over a 3 cm×25 cm column of Amberlite IR 120 (plus) ion exchange resin in the pyridinium salt form (Aldrich Chemical Co.). Upon elution with distilled water, the fractions showing absorbance at 260 nm. were combined and lyophilized. A portion of the resulting mono pyridinium salt (1 g, 2.3 mmol) was dissolved in 100 ml of CHCl$_3$ (dried over Al$_2$O$_3$). The resulting solution was placed in a large cylindrical tube and treated with 5, 10, 15, 20-tetraphenyl-21H, 23H-porphine (2 mg. in 1 ml of CHCl$_3$). The homogeneous green solution was cooled to 0° and pre-saturated with oxygen gas via a sparger tube. The mixture was irradiated under constant O$_2$ flow in a silvered Dewar flask which also contained a cooled immersion well surrounding a 250 watt sodium vapor lamp which was filtered by a single sheet (5 mil) of DuPont Kapton® polyimide film. The temperature in the Dewar remained at 0°–5° C. during a 12 minute irradiation. The solvent was removed in vacuo followed by the addition of 100 ml of distilled water containing 500 mg of NaHCO$_3$. The resulting light pink solution was cooled and filtered through a 0.45 micron Teflon® membrane. The resulting aqueous solution of dioxetane was subjected to a CH$_3$CN—H$_2$O gradient on a polystyrene chromatography column, followed by a second pass with a CH$_3$CN—H$_2$O gradient. The resulting solution, which was free of inorganic salts, was lyophilized to produce 800 mg of a granular, faintly yellow, white solid.

This solid did not exhibit a melting point. Instead, decomposition to give adamantanone as a subliming vapor occurred between 145°–150° C. A solid residue remained which partially decomposed, but did not melt below 270° C.

$^1$H N.M.R. (D$_2$O): δ 85–δ1.75 (m, 12H includes 2 doublets at 0.85, 1H and 1.13, 1H); δ 2.15 (s, 1H); δ 2.75 (s, 1H); δ 3.10 (s, 3H); δ 7.10–δ7.35 (m, 4H). $^{31}$P N.M.R. (D$_2$O; p.p.m. vs H$_3$PO$_4$) δ 1.53, singlet. $^{13}$C-NMR (400 MHz, D$_2$O, p.p.m.): 25.52, 25.68, 31.13, 31.55, 32.13, 32.61, 32.98, 34.20, 35.68, 50.31, 98.49 (dioxetane), 113.61 (dioxetane), 120.95 (broad, low intensity), 121.54, 122.10 (broad, low intensity), 129.37, 134.56, 154.29.

When the experiment was repeated (300 MHz in D$_2$O at 30° C.), the broadened lines sharpened and became more intense relative to the line appearing between them. The sharpened resonances appeared at 120.65 and 121.99 p.p.m. This behavior is a clear indication of restricted rotation of the aromatic group.

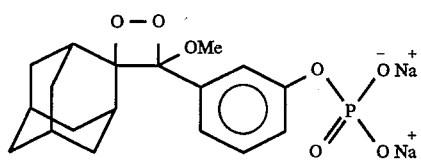

I.R. (Nujol mull): 1600 cm$^{-1}$ (weak), 1580 cm$^{-1}$, 1285 cm$^{-1}$, 1275 cm$^{-1}$, 1120 cm$^{-1}$ (broad), 980 cm$^{-1}$, 895 cm$^{-1}$.

EXAMPLE 7

Methoxy(3-acetoxyphenyl)methylene adamantane

A quantity (1 g, 0.0037 mole) of (3-hydroxyphenyl) methoxymethylene adamantane, obtained according to Example 3, was suspended in 45 ml of CH$_2$Cl$_2$ under argon. The mixture was stirred while adding triethylamine (0.6 ml, 0.0043 mole) whereby a colorless solution was formed. Acetic anhydride (0.4 ml, 0.0043 mole) was then added dropwise. The solution was stirred at room temperature for 48 hours followed by refluxing for 4 hours. The solvent was removed prior to the addition of 40 ml of ether and a small amount of activated carbon. Filtration through Celite and concentration of the filtrate yielded 1.25 g of an oil which was chromatographed through a small column of silica gel (35 g) using CH$_2$Cl$_2$: hexanes (50:50) as eluant. The product (0.800 g) was a colorless oil which was homogeneous on TLC (R$_f$ 0.32; Whatman K5F, CH$_2$Cl$_2$: hexanes, 50:50). I.R. (film): 2900 cm$^{-1}$, 1200 cm$^{-1}$, 1040 cm$^{-1}$, 1035 cm$^{-1}$. $^1$H-NMR (acetone-d6): δ 1.9–2.2 (m, 12H), δ 2.45 (s, 3H), δ 2.85 (s, 1H), δ 3.45 (overlapping singlets 3H & 1H), δ 7.2–7.7 (m, 4H). These data confirmed that the structure of the product was:

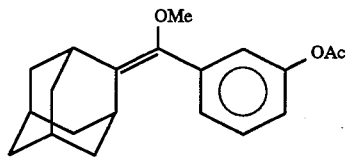

EXAMPLE 8

Synthesis of 3-(2'-spiroadamantane)-4-methoxy-4-(3"-acetoxy)phenyl-1,2-dioxetane A quantity (0.031 g, 0.0001 mole) of (3-acetoxyphenyl)-methoxymethylene adamantane, obtained according to Example 7, was dissolved in 19.4 ml of molecular sieve-dried acetonitrile. A 10 ml portion of this 5.0 mM solution and Rose Bengal immobilized on polystyrene beads ("Sensitox") (0.160 g supplied by Polysciences) were placed in a test tube. The tube was placed at the inside edge of a transparent Dewar flask filled with ice Water. A flow of dry oxygen was initiated through a capillary which extended to the bottom of the tube. The sample was then irradiated with a 250 watt, high pressure sodium lamp at a distance of 3 inches [7.62 cm] from the outer edge of the flask. The disappearance of the band at 260 nm in the UV spectrum was monitored over a 3-hour period. After removal Of the sensitizer, the slightly yellow solution was concentrated and chromatographed on a reverse phase, C18 preparative MPLC column using 60% acetonitrile/water to 100% acetonitrile gradient. Evaporation of the appropriate fractions provided the dioxetanes as an oil. ¹HNMR (acetone-d6): δ 1.2–2.1 (m, 12H), δ 2.3(s,1H), δ 2.4 (s, 3H), δ 3.15 (s, 1H), δ 3.35 (s, 3H), δ 7.3–7.8 (m, 4H). These data confirmed that the structure of the product was:

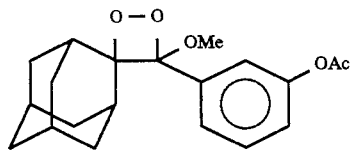

EXAMPLE 9

3-(2'-spiroadamantane)-4-methoxy-4-(3"-hydroxy) phenyl-1,2-dioxetane

A solution of methoxy(3-hydroxyphenyl)methylene adamantane from Example 3 (230 mg, 85 mmol), in 25 ml of dry chloroform, was treated with 0.67 mg purified methylene blue dye. The solution was photooxygenated as described for seven minutes. TLC (K5F; 5% ethyl acetate-dichloromethane) revealed that the starting material (Rf 0.46) had been completely converted to a weakly absorbing (short wave UV) product (Rf 0.55) which was chemiluminescent upon heating the plate to 180° C. The solution was concentrated in vacuo and flash chromatographed on a short column of silica gel (3.5 cm×10 cm) with 2.5% ethyl acetate An dichloromethane as eluant. The appropriate fractions were rotary evaporated to a slightly yellow oil. Trituration at 0° C. with 5% ethyl ether An hexanes afforded 150 mg of the dioxetane as a yellow tinged, white solid which softened at 115° C. and melted between 118°–121° C. (rapid temperature ramp).

I.R. (CHCl$_3$, cm$^{-1}$): 3590, 3360 (broad), 3000, 2920, 2855, 1597, 1588, 1448, 1290, 1175, 1066, 954, 870, 854, 710.

¹H-NMR (400 MHz, CDCl$_3$): δ 1.03–1.90 (m, 12H; includes two doublets at 1.05, 1H and 1.25, 1H); 2.22 (s, 1H); 3.04 (s, 1H); 3.23 (s, 3H); 5.28 (br. s, 1H); 6.98–7.32 (m, 4H).

These data are consistent with the structure as follows:

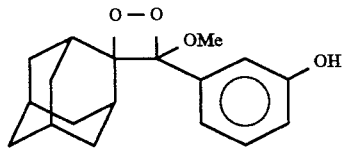

EXAMPLE 10

3-(2'-spiroadamantane)-4-methoxy-4-(3"-acetoxy) phenyl-1,2-dioxetane (3-acetoxyphenyl) methoxymethylene adamantane (1.15 g., 3.68 mmol.) was dissolved in 100 ml of CHCl$_3$ (dried over Al$_2$O$_3$). The solution was placed in a large cylindrical tube and treated with 0.3 ml of a saturated solution of purified methylene blue in CHCl$_3$. The homogeneous blue solution was cooled to 0° and presaturated with oxygen gas via a sparger tube. The mixture was irradiated under constant O$_2$ flow in a silvered Dewar flask which also contained a cooled immersion well surrounding a 250 watt sodium vapor lamp which was filtered by a single sheet (5 mil.) of DuPont Kapton polyimide film. The temperature in the Dewar remained at 0°–5° during a seven minute irradiation. T.L.C. (Whatman K5F, 50:50 CH$_2$Cl$_2$—hexanes) showed no starting material, and product at R$_f$ 0.35. The solvent was removed to yield a blue oil. Upon dissolution in 20 ml of 50:50 CH$_2$Cl$_2$—hexane, some precipitation of a dark solid occurred. The suspension was applied to a 8 g. column of fine mesh silica gel. Elution under pressure with 100 ml of the same solvent yielded 1.3 g. of a light yellow oil upon concentration in vacuo.

¹H-N.M.R. (CDCl$_3$): δ 0.98–δ1.90 (m, 12H); δ 2.15 (s, 1H); δ 2.30 (s, 3H); δ 3.04 (s, 1H); δ 3.20 (s,3H); δ 7.10–δ 7.50 (m, 4H).

A portion of the oily product, when stored at 0°–4° C., slowly solidified over three weeks. Trituration with petroleum ether (B.P. 30°–60° C.) at –20° gave a white solid with a slightly yellow tinge; m.p. 78°–81° C.

I.R. (CHCl$_3$): 3100 cm$^{-1}$, 2920 cm$^{-1}$ 1, 2880 cm$^{-1}$, 1760 cm$^{-1}$ (C=O), 1605 cm$^{-1}$ (weak), 1585 cm$^{-1}$, 1370 cm$^{-1}$, 1190 cm$^{-1}$, 1010 cm$^{-1}$, 910 cm$^{-1}$, 900 cm.

EXAMPLE 11

6-Methoxynaphth-2-yl adamant-2'-yl ketone

Magnesium turnings (1.1 g, 0.045 mol) were placed in a flame-dried flask under argon together with a crystal of iodine and 5 ml of dry THF. The suspension was heated to 45° C., while a solution of 2-bromo-6-methoxynapthalene (7.13 g, 0.03 mol) in 25 ml of dry THF was added dropwise. When the exothermic reaction began, the flask was submerged in a water bath at room temperature. After the addition was completed, the reaction mixture was refluxed for 30 minutes. A solution of 2-cyanoadamantane (4.85 g, 0.03 mol) was added dropwise over a period of 30 minutes. The resulting golden brown solution was refluxed overnight, cooled in an ice bath, and diluted with 30 ml of ether. Concentrated HCl (5 ml, 0.06 mol) was then added dropwise with stirring. The resulting precipitate was separated by filtration, washed with ether, dried, suspended in a mixture of 35 ml of methoxyethanol and 30 ml of concentrated hydrochloric acid, and refluxed for 5 hours. The solid was collected by filtration while the suspension was still warm, then washed with water. The crude ketone (7.3 g) was obtained as an off-white powder. TLC (R$_f$ 0.39; Whatman K5F, CH$_2$Cl$_2$: hexanes, 40:60) indicated one major product. Recrystallization from 150 ml of ethyl acetate yielded 5 g of buff-colored needles (m.p. 173°–75° C). I.R. (CH$_2$Cl$_2$): 2900 cm$^{-1}$, 1665 cm$^{-1}$ (C=O), 1620 cm$^{-1}$, 1475 cm$^{-1}$, 1190 cm$^{-1}$, 1165 cm$^{-1}$. ¹H-NMR (400 MHz, CDCl$_3$) δ 1.56–2.11 (m, 12H); 2.36 (s, 2H); 3.58 (s, 1H ); 3.94 (s, 3H); 7.10–8.26 (m, 6H). The structure of the product was confirmed as:

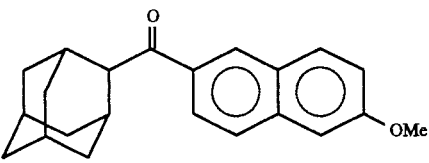

EXAMPLE 12

(6-Methoxynaphth-2-yl)methoxymethylene adamantane

A quantity (3.5 g, 0.011 mol) of 6-methoxynaphth-2-yl adamant-2'-yl ketone, obtained according to Example 11, was suspended in 30 ml of sieve-dried (3 Å) DMSO under argon. Potassium tert-butoxide (2.25 g, 0.0202 mol) was added with stirring to give a deep orange solution containing some solid. The flask was placed in a water bath at 48° C. and dimethyl sulfate (1.9 ml, 0.020 mol) added dropwise by syringe over a period of 20 minutes. The decolorized solution was allowed to cool to room temperature and the resulting suspension was stirred overnight. The mixture was cooled in an ice bath and treated dropwise with 10 ml of water. Stirring was continued in the cold for 45 minutes. The precipitate was separated by filtration and dried by suction before being washed liberally with water. After drying, a white solid (3.45 g, 94%) was obtained having a melting point of 78°–80° C. TLC indicated ($R_f$ 0.64; E. Merck $Al_2O$·hexanes: $CH_2Cl_2$, 60:40) one homogeneous product along with a trace of starting material. I.R. ($CH_2Cl_2$) 2900 $cm^{-1}$, 1620 $cm^{-1}$, 1600 $cm^{-1}$, 1480 $cm^{-1}$, 1030 $cm^{-1}$, $^1$H-NMR ($CDCl_3$): δ 1.80–2.00 (m, 12H); 2.69 (s, 1H); 3.30 (s, 1H); 3.32 (s, 3H); 3.92 (s, 3H); 7.13–7.73 (m, 6H) and confirmed that the structure of the product was:

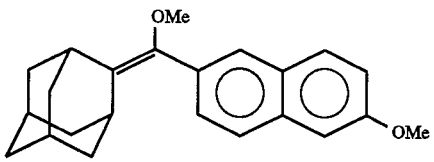

EXAMPLE 13

(6-Hydroxynaphth-2-yl)methoxymethylene adamantane

A solution of (6-methoxynaphth-2-yl) methoxymethylene adamantane (2.0 g, 0.066 mol), obtained according to Example 12, in 20 ml of dry DMF was added to a solution of sodium ethanethiolate (1.0 g, 0.012 mol) in 20 ml of the same solvent under an inert atmosphere. The mixture was refluxed for 2.5 hours. Upon cooling in an ice bath, 150 ml of saturated $NH_4Cl$ was added to the yellow suspension with vigorous stirring. Ethyl acetate (50 ml) and 20 ml of water are then added. After stirring for 10 minutes, the ethyl acetate layer was removed, and the aqueous layer extracted with an additional 50 ml of the same solvent. The combined organic extracts were washed with four 20 ml portions of water and once with 50 ml of saturated aqueous NaCl solution. The solution was dried quickly over $Na_2SO_4$, and concentrated to an orange gum, which was then triturated several times with hexanes. The gum solidified upon storage in a refrigerator to provide 1.7 g of an off-white solid (m.p. 133°–140° C.). An analytical sample melted at 142°–144° C. after recrystallization from $CH_3CN$. TLC (E. Merck $Al_2O_3$, $CH_2Cl_2$: hexanes, 50:50) showed the product naphthol at the origin, while the starting material ($R_f$ 0.85) was absent. $^1$H-NMR (400 MHz, $CDCl_3$): δ 1.79–1.97 (m, 12H); 2.68 (s, 1H); 3.30 (s, 1H); 3.32 (s, 3H); 7.08–7.73 (m, 6H); (OH proton exhibited variable chemical shift). I.R. ($CHCl_3$, $cm^{-1}$): 3580, 3300 (broad), 3000, 2900, 2840, 1625, 1600, 1475, 1442, 1385, 1280, 1170, 1078, 1085, 900, 880, 810. These data confirm that the structure of the product was:

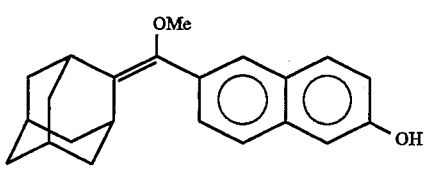

EXAMPLE 14

(6-Acetoxynaphth-2-yl)methoxymethylene adamantane

A quantity (0.7 g, 0.00218 mole) of the crude naphthol enol ether, obtained according to Example 13, was stirred with 20 ml of $CH_2Cl_2$ under argon. Triethylamine (0.35 ml, 0.0025 mole) was added to form a light yellow solution. Acetic anhydride (0.24 ml, 0.0025 mole) was then added dropwise. The mixture was refluxed for 24 hours and stripped in vacuo to produce an oil which was then dissolved in 30 ml of ether and extracted with water (2×15 ml), saturated aqueous sodium bicarbonate solution (1×15 ml) and saturated aqueous sodium chloride solution (1×20 ml). The organic layer was dried quickly over $Na_2SO_4$, followed by rotary evaporation to a light yellow oil which slowly solidified. The solid was triturated twice with hexanes at 0° C. to produce 300 mg of a white solid (m.p. 101°–103° C.). I.R. ($CH_2Cl_2$): 2900 $cm^{-1}$, 1769 $cm^{-1}$ (C=O), 1600 $cm^{-1}$, 1365 $cm^{-1}$, 1205 $cm^{-1}$, 1010 $cm^{-1}$ and $^1$H-NMR (400 MHz, $CDCl_3$): δ 1.79–1.97 (m, 12H); 2.34 (s, 3H); 2.66 (s, 1H); 3.30 (s, 1H+3H); 7.19–7.83 (m, 6H). These data confirmed that the structure of the product was:

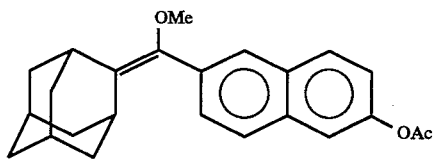

EXAMPLE 15

3-(2'-spiroadamantane)-4-methoxy-4-(6"-acetoxynaphth-2'-yl-1,2-dioxetane

Methoxy(6-acetoxynaphth-2-yl)methylene adamantane from Example 14 was photooxygenated in the same manner as described in Example 8 above. The resulting 3-(2'-spiroadamantane)-4-methoxy-4-(6"-acetoxy)naphth-2'-yl-1,2-dioxetane, after purification by column chromatography, exhibited the following IR and N.M.R. spectra:

I.R. ($CHCl_3$, $cm^{-1}$): 2918, 2856, 1755 (C=O), 1605, 1474, 1453, 1372, 1194, 1173, 1070, 925, 913, 897.

$^1$H-N.M.R. ($CDCl_3$, p.p.m.): 0.95–2.0 (m, 1H -includes 2 doublets at 0.95, 1H, and 1.18, 1H.); 2.19 (s, 1H); 2.38 (s, 3H); 3.10 (s, 1H); 3.24 (s, 3H); 7.30–7.96 (m, 6H). These data confirm the structure as being:

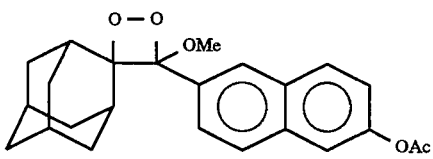

One hundred μl of a $5×10^{-3}$M solution of this dioxetane in acetonitrile was placed in a cuvette, followed quickly by the addition of 2 ml of 75 mM NaOH solution. The slightly cloudy solution was placed in a Spex Fluorolog Fluorometer and light emission accumulated over 5 successive scans from 400 to 700 nm. at room temperature. This experiment was then repeated exactly using a $5\times10^{-3}$M acetonitrile solution of the corresponding 2,7-substituted dioxetane. The chemiluminescent emission spectra of the two dioxetanes were plotted simultaneously as intensity vs. wavelength. The emission from the 2,7-isomer in this predominately aqueous experiment occurred at 555 nm while the less intense emission from the 2,6-isomer occurred at 459 nm An the same medium.

An identical experiment was then performed comparing the emission from 3-(2'-spiroadamantane-4-methoxy-4-(7"-acetoxy)naphth-2'-yl-1,2-dioxetane and 3-(2'-spiroadamantane)-4-methoxy-4-(3"-acetoxy)phenyl-1,2-dioxetane) as $5\times10^{-3}$M solutions in $CH_3CN$. The naphthalene based system emitted light at 555 nm, while the acetoxyphenyl dioxetane did so at 473 nm. with similar intensity.

EXAMPLE 16

Disodium methoxy[(7-phosphoryloxy-)naphth-2-yl] methylene adamantane

Sodium hydride (50% in mineral oil, 240 mg, 6 mmol) was added under an argon atmosphere to methoxy[(7-hydroxy)naphth-2-yl]methylene adamantane (1.45 g, 4.5 mmol) dissolved in sieve-dried DMF (15 ml). The starting compound is from Edwards, et al., co pending and commonly-assigned U.S. Ser. No. 213,672, filed Jun. 30, 1988, Example I. The solution was stirred for 10 min. at room temperature to allow complete sodium naphthoxide formation and then cooled to 0° C., at which time 540 µl (5.87 mmol) of 2-chloro-2-oxo-1,3,2-dioxaphospholane (Fluka) were added dropwise to the suspension. The reaction mixture was slowly warmed to room temperature over 15 min. to ensure formation of methoxy[7-(2-oxo-1,3,2-dioxaphospholan-2-oxy)naphth-2-yl]methylene adamantane. Vacuum-dried sodium cyanide (648 mg, 13.2 mmol) was added as a powder, under argon, followed by stirring at room temperature for 1 hour to effect in situ ring opening of the cyclic phosphate ester. Upon completion of the reaction by TLC analysis (silica gel, 20% EtOAc/hexanes and 30% MeOH/EtOAc) of the reaction products, the solvent was stripped in vacuo while warming gently. The crude monosodium methoxy[(7-[2-cyanoethyl]phosphoryloxy)naphth-2-yl]methylene adamantane was dissolved in 7M $NH_4OH$ (10 ml) and stirred for 15 hours at 40° C. As the reaction proceeded, the product precipitated as a light yellow gum. The aqueous solution, still containing desired naphthyl phosphate, was drawn off and lyophilized to a brown powder after adding 564 mg (6.7 mmol) of $NaHCO_3$. The freeze-dried powder and the gummy precipitate were dissolved together in minimal MeOH and then precipitated as flocculent, tan crystals upon addition of acetonitrile. The precipitate was collected in a Buchner funnel, washed with acetonitrile and dried. Evaporation of the filtrate to a small volume followed by addition of $CH_3CN$ precipitated more naphthyl phosphate, which web collected and washed as described above. This procedure was repeated two times to remove all of the crude phosphate from the filtrate. The dried crystal cake was purified by preparative HPLC, using an $CH_3CN/H_2O$ gradient through a polystyrene column (PLRP-S, Polymer Labora=Dries). The product fractions were combined and lyophilized to yield 572 mg (28%) of disodium methoxy[(7-phosphoryloxy)naphth-2-yl] methylene adamantane as a white, fluffy powder.

$^1$H-NMR ($D_2O$, p.p.m.): 1.60–1.83 (12H, m); 2.46 (1H, d, J=97 Hz); 3.02 (1H, br. s); 3.22 (3H, s); 7.20 (1H, d, J=8.43 Hz); 7.29 (1H, d, J=9.28 Hz); 7.51 (1H, s); 7.65 (1H, s); 7.72 (2H, m).

$^{31}$NMR ($D_2O$, 85% $H_3PO_4$ std., p.p.m.): 0.99 (1P).

EXAMPLE 17

Disodium 3(2'-spiroadamantane)-4-methoxy-4-(7"-phosphoryloxy)naphth-2"-yl-1,2-dioxetane A solution of disodium methoxy[(7-phosphoryloxy) naphth-2-yl]methylene adamantane (18.8 mg, 0.042 mmol) and 5,10,15,20-tetraphenyl-21H,23H-porphine (TPP, 20 µl of a 2% solution in $CHCl_3$ by weight) in 2% $MeOH/CHCl_3$ (10 ml) was irradiated with a 250 W, high pressure sodium lamp at 10° C. while passing a stream of oxygen through the solution. A 5 mil. thick piece of Kapton® polyimide film (DuPont) placed between the lamp and the reaction mixture filtered out unwanted UV radiation. Analytical HPLC (UV detector at 254 nm) showed complete dioxetane formation after irradiating 10.5 minutes. The reaction was also followed by UV spectroscopy with absorption at 255 nm due to the conjugated vinyl group disappearing upon photoxygenation. The dioxetane showed one major UV absorption at 230 nm. After evaporating the chloroform at 0° C., the residue was dissolved in ice water, passed through a 0.46 µ filter, and separated by preparative HPLC on a polystyrene column with an acetonitrile/water gradient. The fractions were frozen and lyophilized at 0° C., yielding 12.1 mg (60%) of the disodium phosphate dioxetane as a white, fluffy powder.

$^1$H-NMR ($D_2O$, p.p.m.): 0.69 (1H, d); 0.98 (1H, d); 1.34–1.80 (10H, m); 2.11 (1H, d, J=1.35 Hz); 2.77 (1H, d, J=1.96 Hz); 3.08 (3H, s); 7.31–7.98 (6H, m).

These data confirm tile structure to be as follows:

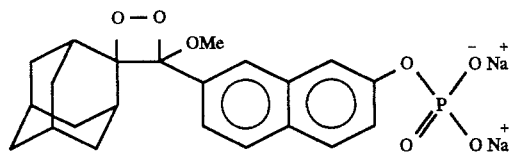

9.5 µl of a 0.4 mM solution of the above dioxetane in a pH 9 carbonate buffer (0.05M) was added to 490 µl of the same buffer in a glass tube. This solution was treated with $4\times10^{-14}$ moles of dialyzed alkaline phosphatase (Biozyme; ALPI-11G) in 5 µl of deionized water. The tube was placed in a luminometer (Turner 20E) at 29° C. to reveal constant green light emission for over 60 minutes.

EXAMPLE 18

3-(Adamantylidenemethoxymethyl)phenyl β-D-galactopyranoside tetraacetate

To a solution of methoxy (3-hydroxyphenyl) methyleneadamantane (1.21 g, 4.48 mmole) from Example 3 in 20 ml of molecular sieve-dried (3 Å) N,N-dimethylformamide was slowly added with stirring 0.188 g (4.7 mmole, Aldrich) of 60% NaH under argon at room temperature. Hydrogen evolution occurred immediately as the slightly yellow precipitate of sodium phenoxide formed. After stirring 30 minutes at room temperature, the suspension was treated with 2,3,4,6-tetra-O-acetyl-β-D-galactopyranosyl bromide (1.987 g, 4.8 mmole), obtained by following the procedure of R. W. Jeanloz and P. J. Stoffyn (*Methods Carbohydr. Chem.*, 1: 221–227 (1962). The resulting orange, homogeneous solution was stirred for three days at room temperature and then poured into water (400 ml). The mixture was extracted with 30% EtOAc in hexanes (3×120 ml), dried and concentrated to give 2.96 g of crude reaction product.

The crude product were separated into two fractions by the filtration through a short silica gel column, eluting with 25–40% EtOAc in hexanes. The less polar mixture (1.05 g) contained mainly the enol ether starting material and a small amount of methoxy(3-acetoxyphenyl) methyleneadamantane. The Rf values on TLC.(Whatman K5F; 30% EtOAc in hexane) were 0.64 and 0.76 respectively. This mixture could be treated with NaOMe in MeOH to regenerate the starting material, which was recycled.

The more polar mixture (1.06 g) was composed of the desired aryl glycoside (Rf=0.40) and β-elimination product (galactal, Rf=0.36) from acetobromogalactose and was used for the subsequent deacetylation reaction without further purification.

A spectroscopic sample of aryl β-D-galactopyranoside tetraacetate (purity>85%) was obtained from preparative TLC as a gum. IR (CHCl₃): 3020, 2908, 3842, 1748 (acetates), 1596, 1575, 1368, 1230 and 1078 cm⁻¹; ¹H-NMR (400 MHz, CDCl₃): δ 1.7 –2.0 (12H, m, adamantane), 2.01 (3H, S, OAc), 2.06 (3H, s, OAc), 2.07 (3H, s, OAc), 2.18 (3H, s, OAc), 2.64 (1H, br. s, H-1'b), 3.24 (1H, br.s, H-1'a), 3.28 (3H, s, OMe), 4.07 (1H, t, J=6.7 Hz, H-5), 4.21 (2H, d, J=6.7 Hz, H-6), 5.05 (1H, d, J=7.6 Hz, H-1), 5.11 (1H, dd, J=10.6, 3.2 Hz, H-3), 5.46 (1H, d, J=3.2Hz, H-4), 5.50 (1H, dd, J=10.6, 7.6 Hz, H-2), 6.92 (1H, br. d, J=8 Hz, H-4" or H-6"), 6.97 (1H, br. s, H-2"), 7.02 (1H, br. d, J=7.8 Hz, H-6" or H-4") and 7.26 p.p.m. (1H, dd, J=8.0, 7.8 Hz, H-5"). The 7.6 Hz coupling constant for J (1,2) indicates a glycoside having the β configuration. These data confirmed that the structure of the product was:

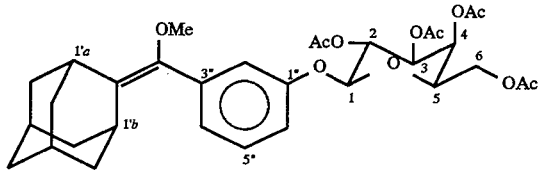

EXAMPLE 19

3-(Adamantylidenemethoxymethyl) phenyl-β-D-galactopyranoside

A solution of the polar mixture (1.06 g), obtained from Example 18 in 10 ml of MeOH, was treated with excess NaOMe in MeOH (0.75 ml, Aldrich) under argon. After stirring overnight at room temperature, the reaction was quenched with solid NH₄Cl (0.7 g) at room temperature and then stirred for 30 minutes. After rotary evaporation of the methanol, the residue was triturated with CHCl₃ and filtered through sand. The solid was washed with additional CHCl₃ until TLC showed that no additional U.V. absorbing product was eluted. The combined organic solution was concentrated to give a yellow gum which was then filtered through a short silica gel column, eluting with 5–10% MeOH in chloroform, to afford 0.383 g of yellow gum (Rf=0.25; K5F: 10% MeOH-CHCl₃) with an overall yield of 17–20% from methoxy (3-hydroxyphenyl)methyleneadamantane. IR (CHCl₃): 3010 (OH), 2996, 2904, 2820, 1595, 1574 and 1078 cm⁻¹; ¹H-NMR (400 MHz, CDCl₃): δ 1.65–1.95 (12H, m, adamantane), 2.61 (1H, br. s, H-1'b), 3.18 (1H, br. s, H-1'a), 3.23 (3H, s, OMe), 3.62 (1H, m, H-5), 3.81 (3H, m, H-3 and H-6), 4.03 (1H, dd, J=9, 8.3 Mz, H-2), 4.19 (1H, br.s, H-4), 4.89 (1H, d, J=7.6 Hz, H-1), 6.88–6.95 (2H, m, H-4" and H-6"), 6.99 (1H, s, H-2") and 7.15 ppm (1H, t, J=7.8 Hz, H-5"). These data confirmed that the structure of the product was:

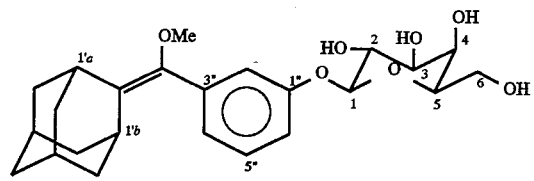

An analytical sample, obtained from reverse phase preparative HPLC, exhibited a broad melting point range; sintering at 50°–55° to form a contracted column which became translucent at 89°, and almost transparent from 96°–99°. The column became transparent at 105°, but still retained its physical integrity. At 117°–120° the material collapsed against the glass tube as a viscous, non-mobile melt.

EXAMPLE 20

3-(2'-Spiroadamantane)-4-methoxy-4-(3"-β-D-galactopyranosyloxyphenyl)1,2-dioxetane In a culture tube, 75.1 mg (0.17 mmole) of the enol ether galactoside obtained from Example 19 was dissolved in 12 ml of 5% MeOH in CHCl₃. A quantity (0.6 mg) of 5,10,15, 20-tetraphenyl-21H, 23H-porphine (TPP) was added as a sensitizer to form a homogenous violet solution. The mixture was saturated with a stream of dry oxygen through a capillary tube and placed in a silvered Dewar flask containing a 250-watt high pressure sodium lamp inside a water-cooled immersion well. A piece of 5 mil. Kapton® (DuPont) was placed inside the well as a UV filter. Ice water was pumped through the apparatus to maintain the sample temperature below 10° C. The solution was irradiated for 10 minutes under constant O₂ flow, during which time the U.V. absorption at 261 nm (CHCl₃) of the starting material disappeared and a new peak at 272 nm with a shoulder at 278 nm appeared. The solvent was evaporated at low temperature and the residue was triturated with 30% CH₃CN in H₂O. The aqueous sample was filtered through a 0.45 micron nylon filter and chromatographed on a reverse phase preparative HPLC column using a water-acetonitrile gradient. After lyophilization the dioxetane was collected as a white, cotton-like powder in good yield. In a melting point capillary tube, the product began to sinter at 97° and proceeded with significant volume loss between 102° and 107°. The powder became moist at 110°, finally producing a clear sticky gum at 118° C. IR (CHCl$_3$): 3390 (OH), 3000, 2914, 2854, 1582, 3284, 1272, and 1068 cm$^{-1}$; $^1$H-NMR (400 MHz, CDCl$_3$): δ 0.95–2.07 (13H, m), 2.97 (1H, br.s), 3.11 and 3.13 (3H, two s, OMe), 3.65 (1H, br.s), 3.82 (3H, br.s), 4.05 (1H, t, J=7.22 Hz), 4.22 (1H, br.s), 4.89 (1H, d, J=7.3 Hz), and 7.01–7.28 ppm (4H, m). These data confirm the following structure for the dioxetane product, which exists as a mixture of two diastereomers at C-4:

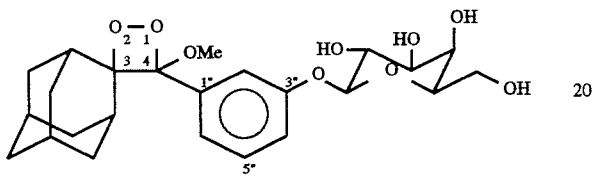

What is claimed is:

1. A compound of the formula:

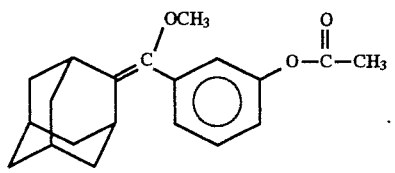

2. A compound of the formula

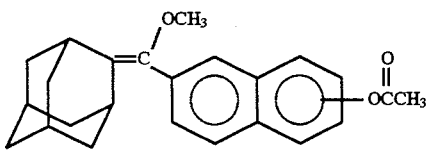

* * * * *

UNITED STATES PATENT AND TRADEMARK OFFICE
CERTIFICATE OF CORRECTION

PATENT NO. : 5,639,907
DATED : June 17, 1997
INVENTOR(S) : Irena Bronstein, et al It is certified that error appears in the above-identified patent and that said Letters Patent is hereby corrected as shown below:

Cover Page, Title [54], " THEREFOR" should read -- THEREOF --.

Column 1, line 17, "enzyme-clearable" should read -- enzyme-cleavable --.

Column 1, line 60, "1,2-dioxetane-B" should read -- 1,2-dioxetanes --.

Column 2, line 26, "ketones quite" should read -- ketone is quite --.

Column 2, line 47, "dryl" should read -- aryl --.

Column 2, line 53, "an Amine" should read -- an imine --.

Column 3, line 21, "an arl group" should read -- an aryl group --.

Column 5, line 12, "enzyme-clearable" should read -- enzyme-cleavable --.

Column 5, line 23, "enzyme-clearable groups include enzyme-clearable" should read -- enzyme-cleavable groups include enzyme-cleavable --.

Column 5, line 45, "bond clearable" should read -- bond cleavable --.
Column 6, line 6, "clearable" should read --cleavable --.
Column 6, line 6, "enzyme clearable" should read -- enzyme cleavable --.

UNITED STATES PATENT AND TRADEMARK OFFICE
CERTIFICATE OF CORRECTION

PATENT NO. : 5,639,907
DATED : June 17, 1997
INVENTOR(S) : Irena Y. Bronstein, et al It is certified that error appears in the above-identified patent and that said Letters Patent is hereby corrected as shown below:

Column 6, structure at end, " 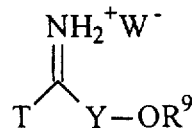

"

should read --

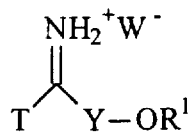

--.

Column 9, line 24, "dimethyl 5 ether" should read -- dimethyl ether --.

Column 15, line 12, "clearable" should read -- cleavable --.

Column 19, line 1, "AMPPD $Na^+NH_4^+$" should read -- AMPPD $Na^+NH_4^+$ --.

UNITED STATES PATENT AND TRADEMARK OFFICE
CERTIFICATE OF CORRECTION

PATENT NO. : 5,639,907
DATED : June 17, 1997
INVENTOR(S) : Irena Bronstein, et al It is certified that error appears in the above-identified patent and that said Letters Patent is hereby corrected as shown below:

Column 21, line 2, "MPLC" should read -- HPLC --.

Column 21, line 32, "An dichloromethane" should read -- in dichloromethane --.

Column 21, line 34, "ether An hexanes" should read -- ether in hexanes --.

Column 25, line 63, "which web collected" should read -- which was collected --.

Column 26, line 2, "Polymer Labora=Dries" should read -- Polymer Laboratories -- .

Signed and Sealed this

Twenty-eighth Day of April, 1998

Attest:

*Attesting Officer*

BRUCE LEHMAN

*Commissioner of Patents and Trademarks*